(12) United States Patent
Lentz et al.

(10) Patent No.: US 8,162,929 B2
(45) Date of Patent: Apr. 24, 2012

(54) CRYOABLATION SEGMENT FOR CREATING LINEAR LESIONS

(75) Inventors: David J. Lentz, La Jolla, CA (US);
Jillian K. Allen, San Diego, CA (US);
Richard J. Koerner, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1331 days.

(21) Appl. No.: 11/757,124

(22) Filed: Jun. 1, 2007

(65) Prior Publication Data

US 2008/0300584 A1    Dec. 4, 2008

(51) Int. Cl.
*A61B 18/18* (2006.01)

(52) U.S. Cl. ............................................ 606/21; 606/20

(58) Field of Classification Search ............... 606/20–26
See application file for complete search history.

(56) References Cited

U.S. PATENT DOCUMENTS

| | | | |
|---|---|---|---|
| 5,759,182 A | 6/1998 | Varney et al. | |
| 5,899,898 A | 5/1999 | Arless et al. | |
| 5,899,899 A | 5/1999 | Arless et al. | |
| 6,235,019 B1 | 5/2001 | Lehmann et al. | |
| 6,251,105 B1 | 6/2001 | Mikus et al. | |
| 6,579,287 B2 | 6/2003 | Wittenberger et al. | |
| 6,602,247 B2 | 8/2003 | Lalonde | |
| 6,905,510 B2 * | 6/2005 | Saab | 607/105 |
| 2002/0183731 A1 * | 12/2002 | Holland et al. | 606/21 |
| 2003/0109912 A1 * | 6/2003 | Joye et al. | 607/113 |
| 2004/0024392 A1 * | 2/2004 | Lewis et al. | 606/22 |
| 2007/0149958 A1 * | 6/2007 | DeLonzor et al. | 606/21 |

* cited by examiner

*Primary Examiner* — Linda Dvorak
*Assistant Examiner* — Amanda Scott
(74) *Attorney, Agent, or Firm* — Seager, Tufte & Wickhem, LLC

(57) ABSTRACT

An applicator for cryoablating tissue to form linear (i.e. straight line and curvilinear) lesions in targeted tissue includes a fluid refrigerant delivery system having a source of a fluid refrigerant and a tubular cryoablation segment. Structurally, the segment has an open proximal end and a distal end, and is formed with a lumen. Also, the segment is formed with at least one distal port and at least one proximal port, with each port connected in fluid communication with the segment's lumen. The proximal end of the tubular segment is operably connected in fluid communication with the source of fluid refrigerant. For the system, the ports can be selectively sized to outflow liquid refrigerant through the distal and proximal ports at a substantially same mass flow rate.

21 Claims, 2 Drawing Sheets

CRYOABLATION SEGMENT FOR CREATING LINEAR LESIONS

FIELD OF THE INVENTION

The present invention pertains generally to systems for ablating tissue using extremely cold temperatures (i.e. cryoablation). More particularly, the present invention pertains to medical applicators including catheters and probes for cryoablating tissue to create linear tissue lesions. The present invention is particularly, but not exclusively, useful for employing a fluid refrigerant to uniformly cryoablate tissue along a line, wherein cooling is accomplished by a phase change in the fluid refrigerant.

BACKGROUND OF THE INVENTION

There are now quite a number of approved medical procedures that involve the ablation or removal of tissue. In particular, many of these procedures are performed by advancing a catheter through the vasculature of a patient to an operational site. Depending on the requirements for the particular procedure, the target tissue that is to be ablated may be characterized as being a single spot, a series of spots or a linear ablation (i.e. a straight line or curvilinear ablation). Further, due to the nature and the anatomical constraints that are imposed on the procedure by the vasculature, each procedure will present unique issues for consideration.

In recent years, various catheters have been proposed for the purpose of ablating tissue in diverse parts of the vasculature. Early devices focused on the use of radiofrequency (rf) energy or ultrasonic energy to ablate internal tissue. More recently, however, it has been determined that cryoablation techniques may be preferable in many applications. Insofar as cryoablation techniques are concerned, a specific issue for consideration involves the control of the necessary temperature conditions in the vasculature. On the one hand, proper temperature conditions must be created in the area where the cryoablation is to occur. On the other hand, these temperature conditions must be confined to the desired area to avoid adversely impacting non-target tissue.

The destruction of tissue by cryoablation requires that the targeted tissue be cooled below a certain temperature. In addition, recent studies have suggested that the cooling rate and subsequent warming rate can affect the percentage of tissue cells destroyed in a cryoablation procedure. For example, co-pending, co-owned U.S. patent application Ser. No. 11/050,974 filed Feb. 4, 2005 and titled "Warming Gradient Control for a Cryoablation Catheter" discloses a regimen of preferred cooling and warming rates to maximize tissue destruction. As such, U.S. patent application Ser. No. 11/050,974 is hereby incorporated by reference herein. It can be appreciated that when these methods are applied to create a linear lesion, it becomes important to ensure that the preferred cooling and warming rates are maintained uniformly along the length of the targeted tissue.

One application in which a linear ablation is currently prescribed is in the treatment of irregular heart rhythms such as atrial fibrillation. Specifically, it is believed that at least one-third of all atrial fibrillation cases are caused by irregular electrical signals that originate in one or more of the four pulmonary veins. It is further believed that the optimal technique for treating atrial fibrillation is to electrically isolate these pulmonary veins by creating a linear, circumferential lesion around each ostia where an affected pulmonary vein connects with the left atrium. To be effective, each linear conduction block must completely block all of the irregular electrical signals and this often requires the ablation of a relatively deep and long, uniform lesion.

To efficiently create a uniform linear lesion such as the one described above, it is typically desirable to simultaneously ablate all of the targeted tissue in a one-step cryoablation process. For this purpose, it is typically necessary to use an element having a contact surface that is shaped (or shapeable at the operational site) to conform to the shape of the desired linear lesion. Along these lines, co-pending, co-owned U.S. patent application Ser. No. 10/876,312 filed Jun. 24, 2004 and titled "Active System for Deflecting a Distal Portion of a Catheter into a Hoop Configuration" discloses a system for contacting and cryoablating a linear circumferential band of internal target tissue in a one-step cooling process. Accordingly, U.S. patent application Ser. No. 10/876,312 is hereby incorporated by reference herein.

When a one-step cooling process is used to ablate a linear lesion, it is often preferable that the operable contact surface be uniformly cooled along its length. In this regard, phase change refrigerants can be used to cool a contact surface by undergoing a liquid to gas phase transition in close proximity to the contact surface. For example, co-owned U.S. Pat. No. 7,004,936 entitled "A Refrigeration Source for a Cryoablation Catheter" discloses a system for delivering a liquid phase change refrigerant to a volume adjacent a contact surface for transition to a gas in the volume to cool the contact surface. Accordingly, U.S. Pat. No. 7,004,936 is hereby incorporated by reference herein. In some cases, when a phase change refrigerant is used to cool a relatively long linear contact surface, it can become necessary to vaporize the liquid refrigerant at more than one point along the length of the contact surface in order to uniformly cool the contact surface.

In light of the above, it is an object of the present invention to provide medical applicators such as catheters and probes for the purposes of cryoablating linear shaped lesions. It is another object of the present invention to provide devices and methods for uniformly cooling a linear contact surface of a contact element to a cryogenic temperature with a phase change refrigerant. Further, it is an object of the present invention to create a linear structure that provides for simultaneous liquid-to-gas phase changes at various locations along the length of the cooling segment. Yet another object of the present invention is to provide devices and methods for cryoablating linear shaped lesions that are easy to use, relatively simple to implement, and comparatively cost effective.

SUMMARY OF THE INVENTION

The present invention is directed to devices and methods for cryoablating tissue to form linear (i.e. straight line and curvilinear) lesions in targeted tissue. More specifically, the present invention includes a fluid refrigerant delivery system for use in a cryoablation applicator. Exemplary applicator types can include, but are not limited to, catheters for ablating internal tissue within the vasculature or other ductal systems of the body and probes for cryoablating exposed tissue.

In an overview of the present invention, the fluid refrigerant delivery system includes a source of fluid refrigerant, and a tube shaped cryoablation segment for receiving the fluid refrigerant. Structurally, the cryoablation segment is a cylindrical, tube-like structure and is preferably made of a flexible polymeric material (e.g. nylon). The segment has an open proximal end and a distal end that may, or may not, be open. In either case, the segment is formed with a lumen that extends at least a portion of the distance from the proximal end toward the distal end, and a plurality of exhaust ports that are in fluid communication with the lumen.

For the delivery system of the present invention, the proximal end of the tubular segment is connected in fluid communication with the source of the fluid refrigerant via a catheter/probe. This connection then allows fluid refrigerant to flow from the source and into the lumen of the segment through its proximal end. An important aspect of the present invention is that the fluid refrigerant (e.g. nitrous oxide ($N_2O$), is preconditioned so that it enters the lumen of the segment at a predetermined temperature, under a predetermined pressure. Preferably, for a $N_2O$ fluid refrigerant, the pre-conditioned state is such that the refrigerant is in a liquid state at a working pressure ($p_w$), that is in a range of approximately 350-500 psia, and it is at a pre-cooled working temperature ($T_w$) of about minus forty degrees Centigrade.

The cryoablation segment of the present invention is formed with at least one distal exhaust port, and at least one proximal exhaust port. Each of these exhaust ports is connected in fluid communication with the segment lumen, and each exhaust port is individually configured and dimensioned. Specifically, each exhaust port in the segment is constructed and dimensioned according to its location in the segment. This is done to establish a substantially same mass flow rate for fluid refrigerant as it exits each of the respective exhaust ports. In addition to creating a substantially same mass flow rate for all exhaust ports, all exhaust ports are engineered to specifically ensure that the fluid refrigerant exits from the most distal exhaust port in a liquid state. Consequentially, the fluid refrigerant will exit all of the exhaust ports in a liquid state. For the specific case wherein the fluid refrigerant is nitrous oxide, it is important that the refrigerant reaches its normal boiling point (i.e. approximately minus eighty eight degrees Centigrade, at one atmosphere of pressure), after it exits from the most distal exhaust port.

With the above in mind, several structural variations and combinations of variations are possible for the cryoablation segment of the present invention. For one, in a comparison between a proximal exhaust port and a more distal exhaust port in the segment, the proximal port will have a diameter "D" that is smaller than the diameter "d" of the more distal exhaust port (d>D). For another variation, a plurality of exhaust ports can be located at a same distance from the proximal end of the segment. Again, however, regardless of their number and their respective location, the mass flow rate of fluid refrigerant through all exhaust ports needs to be essentially the same. Furthermore, whatever pressure drop is caused by a more proximal exhaust port, the cryoablation segment of the present invention must still cause the fluid refrigerant to exit from the most distal exhaust port in a liquid state.

For another variation of the tubular segment, the segment's lumen can be tapered with a decreasing lumen cross-sectional area in the distal direction. As compared with a uniform, non-tapered lumen, the tapered lumen structure results in less pressure drop as the refrigerant transits to the distal exhaust port. Functionally, the tapered lumen can be employed to prevent premature boiling of the refrigerant during its transit through the segment to the distal exhaust port. The result is the simultaneous outflow of liquid refrigerant from both distal and proximal exhaust ports. It is to be appreciated that features of the three embodiments described above can be used alone or in combination.

In use, an element having a contact surface is positioned to surround the segment and thereby establish an expansion chamber between the element and the segment. For example, the segment can be positioned co-axially within a flexible, tubular catheter body to create an expansion chamber in the annular space between the segment and body. Next, the element is placed in contact with a linear portion of tissue. The element is then cooled by flowing liquid refrigerant from the source and through the exhaust ports. After the refrigerant outflows from the exhaust ports into the expansion chamber, the refrigerant transitions from a liquid to a gas, absorbing heat from the surroundings. This heat absorption cools and cryoablates the contacted tissue to create a linear lesion.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
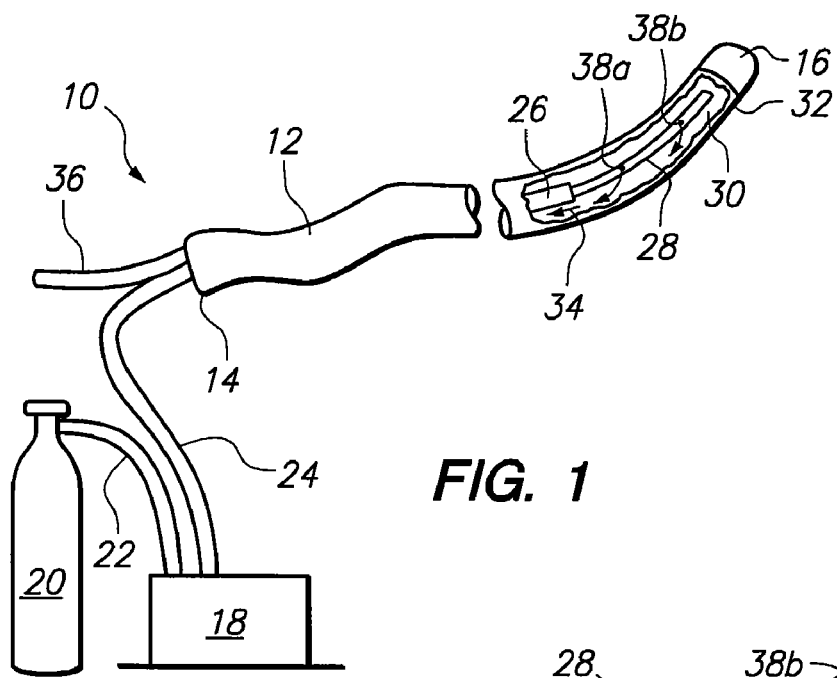
FIG. 1 is a perspective view of a catheter system for cryoablating a linear lesion shown with a portion of the outer catheter body removed to reveal internal details.

Referring initially to FIG. 1, a system for ablating internal target tissue to form linear (i.e. straight line and curvilinear) lesions is shown and generally designated 10. As shown, the system 10 includes an applicator, which for the embodiment shown is a catheter 12. Although the system 10 is described herein for a catheter 12, those skilled in the pertinent art will appreciate that the systems and methods described herein can be implemented with other applicators such as a cryoprobe (not shown) that is configured to contact and ablate exposed tissue.

FIG. 1 further shows that the catheter 12 extends from a proximal end 14 to a distal end 16. Typically, the proximal end 14 remains outside a patient's body during a procedure and is connected to a handle (not shown). In use, the distal end 16 of the catheter 12 is typically inserted into a patient through a peripheral artery, such as the femoral artery, and advanced through the patient's vasculature until the distal end 16 is positioned at a targeted location such as a heart chamber. Although the system 10 is capable of performing a cryoablation procedure in an upper body vessel, such as a pulmonary vein, those skilled in the pertinent art will quickly recognize that the use of the system 10, as herein described, is not limited to use in any one type of vessel, but, instead can be used in vascular conduits and other ductal systems throughout the human body.

FIG. 1 further shows exemplary means for passing a fluid refrigerant through a cryoablation segment, and shows that a refrigerant control unit 18 and a refrigerant tank 20 are provided to supply a refrigerant to the cryotip (i.e. the distal portion) of the catheter 12. In particular, refrigerant from the tank 20 flows to the refrigerant control unit 18 through line 22, as shown. At the refrigerant control unit 18, various valves, pre-cooling circuits, control systems and other components are configured to produce a regulated flow of sub-cooled, liquid refrigerant which is then directed into supply line 24. As shown in FIG. 1, the supply line 24 includes both a supply tube 26 and a cryoablation segment 28. In a typical arrangement, the supply tube 26 is sized to impart a negligible impedance to the flow of refrigerant from the refrigerant control unit 18. On the other hand, for the system 10, the cryoablation segment 28 is typically sized with a much greater impedance than the supply tube 26 to hereby cause most of the supply line pressure drop to occur in the cryoablation segment 28. Functionally, this results in a concentration of cooling power at the cryotip of the catheter 12. In particular, for the case wherein the fluid refrigerant is nitrous oxide ($N_2O$), the refrigerant is preconditioned such that it is in a liquid state at a working pressure ($p_w$), that is in a range of 350-500 psia, and it is precooled to a working temperature ($T_w$) of about −40° C.

From FIG. 1 it can be seen that a distal portion of the supply line 24 is disposed in the lumen 30 of a tubular catheter body 32. With this cooperation of structure, a return line 34 is established in an annular space between the inner surface of the catheter body 32 and the outer surface of the supply line 24. For the system 10, return line 34 is placed in fluid communication with return line 36 allowing exhausted coolant to be recycled, vented or scrubbed. With this cooperation of structure, fluid refrigerant from the refrigerant control unit 18 is directed into the supply line 24. The fluid refrigerant traverses the supply tube 26 and flows into the cryoablation segment 28. Fluid refrigerant then exits the cryoablation segment 28 through side exhaust ports 38a,b and expands in the space between the segment 28 and the catheter body 32 to cool the cryotip.

In addition to the structures shown in FIG. 1, it can be appreciated that the system 10 can include an articulation system to steer the catheter 12 during an advancement of the distal end 16 of the catheter 12 through body conduits, to place the cryotip proximate to the target tissue and to selectively reconfigure the cryotip into a selected shape such as a hoop. A suitable articulation segment for use in the system 10 is disclosed in co-pending, co-owned U.S. patent application Ser. No. 10/223,077, filed on Aug. 16, 2002, and titled "Catheter Having Articulation System." Also, the system 10 can include pressure and temperature sensors for catheter control (not shown) and mapping electrodes (also not shown).

In one embodiment of the system 10, a fluid refrigerant is used that transitions from a liquid state to a gaseous state as it outflows from the cryoablation segment 28 to cool the cryotip. A suitable refrigerant control unit 18 for delivering a refrigerant in a liquid state to a cryoablation segment 28 for transition to a gaseous state during outflow from a supply line is disclosed in co-pending, co-owned U.S. patent application Ser. No. 10/243,997, entitled "A Refrigeration Source for a Cryoablation Catheter" and filed on Sep. 12, 2002. Co-pending U.S. patent application Ser. No. 10/243,997 was previously incorporated by reference herein. Heat absorbed by the refrigerant during the liquid to gas phase transition (i.e. latent heat) cools the cryotip. In one implementation, nitrous oxide is used as the refrigerant with suction applied to the return line 36 allowing the cryotip to be cooled to a temperature of approximately −85 degrees Celsius. For the system 10, a distal portion of the catheter body 32 can be made of a thermally conductive material (e.g. a polymer filled with metal) to allow heat to flow easily between the lumen 30 and the target tissue.

Figure 2:
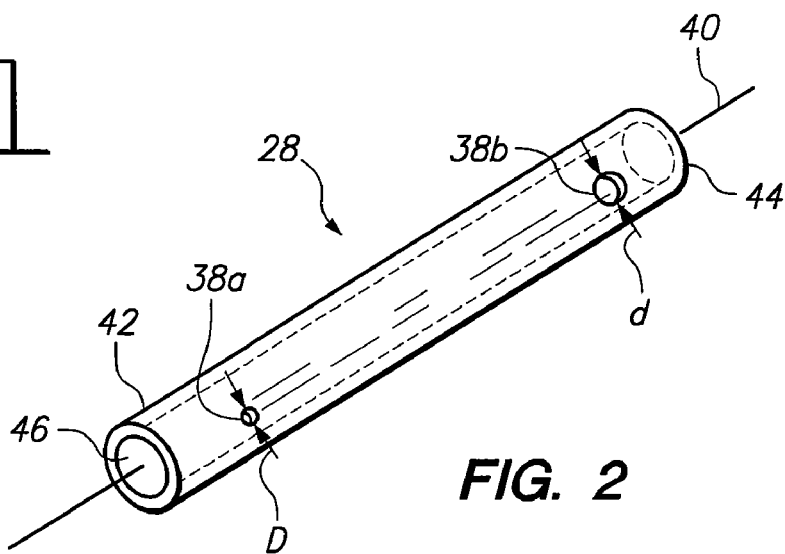
FIG. 2 is a perspective view of a cryoablation segment for use in the catheter shown in FIG. 1.

FIG. 2 shows the cryoablation segment 28 in more detail. Specifically, the segment 28 shown is shaped as an elongated tube that defines a longitudinal axis 40. For the embodiment shown in FIG. 2, the segment 28 extends from an open proximal end 42 to a closed distal end 44 and is formed with a segment lumen 46 that extends a portion of the distance from the proximal end 42 to the distal end 44. For the system 10 shown in FIG. 1, the cryoablation segment 28 is typically made of a flexible polymeric material (e.g. nylon) allowing the segment 28 to bend and reshape together with a flexible distal portion of the catheter body 32 during steering, cryotip placement and articulation. FIG. 2 further shows that the segment 28 is formed with a distal side exhaust port 38b and a proximal side exhaust port 38a and each exhaust port 38a,b is connected in fluid communication with the segment lumen 46. In addition, it can be seen that the proximal side exhaust port 38a has a port diameter, D, and the distal side exhaust port 38b has a port diameter, d, with the proximal port diameter being smaller than the distal port diameter (d>D). Within this constraint, the side exhaust ports 38a,b can be sized to outflow refrigerant through the distal and proximal side exhaust ports 38a,b at a substantially same refrigerant mass flow rate. More specifically, in some cases, the segment 28 can be configured to simultaneously outflow refrigerant from both the distal and proximal side exhaust ports 38a,b while the refrigerant is still in a substantially liquid state (i.e. with little or no vapor present). This allows for uniform cooling along the length of the segment 28.

Figure 3:
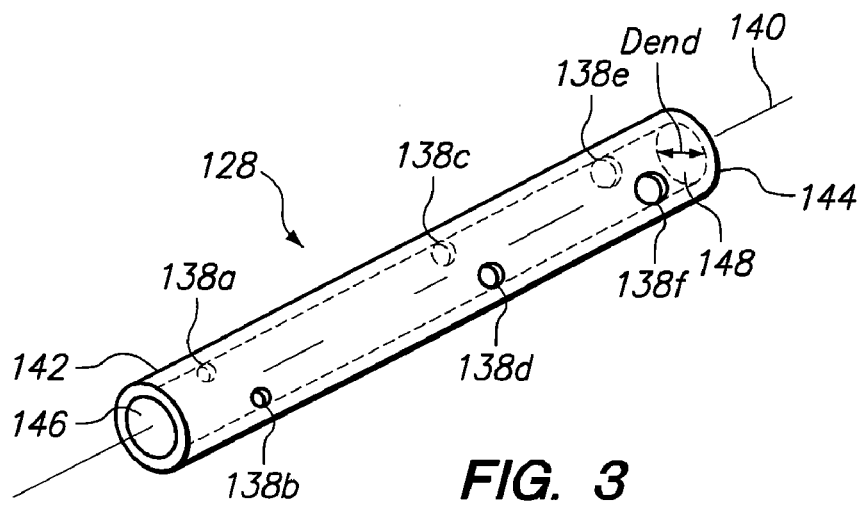
FIG. 3 is a perspective view of another embodiment of a cryoablation segment for use in the catheter shown in FIG. 1 having six side exhaust ports arranged as diametrically opposed pairs and an end exhaust port.

FIG. 3 shows another embodiment of a cryoablation segment (designated segment 128) for use in the system 10 shown in FIG. 1. As shown in FIG. 3, the segment 128 is shaped as an elongated tube that defines a longitudinal axis 140. FIG. 3 also shows that the segment 128 extends from an open proximal end 142 to an open distal end 144 and is formed with a segment lumen 146 that extends from the proximal end 142 to the distal end 144. Like the segment 28 discussed above, the segment 128 is typically made of a flexible polymeric material. FIG. 3 further shows that the segment 128 is formed with six side exhaust ports 138a-f that are arranged as diametrically opposed pairs. There may, of course, be additional pairs of exhaust ports, if desired. In addition, the open distal end 144 of the segment 128 establishes an end exhaust port 148 having a diameter $D_{END}$. As further shown, the side exhaust ports 138a-f and end exhaust port 148 are connected in fluid communication with the segment lumen 146. For the system 10 shown in FIG. 1, the segment 128 shown in FIG. 3 can be configured with the side exhaust ports 138a-f and end port 148 sized to outflow refrigerant through all of the ports (i.e. the ports 138a-f, 148) at a substantially same refrigerant mass flow rate. In a particular embodiment of the cryoablation segment 128, the end exhaust port 148 has a diameter of approximately 0.008 inches, the side exhaust ports 138e and 138f each have a diameter of approximately 0.005 inches, the side exhaust ports 138c and 138d each have a diameter of approximately 0.004 inches, and the side exhaust ports 138a and 138b each have a diameter of approximately 0.003 inches. Moreover, for this particular embodiment, a segment length of approximately two inches is used, with the side exhaust ports 138e and 138f located approximately 0.6 inches from the distal end 144, the side exhaust ports 138c and 138d located approximately 1.2 inches from the distal end 144, and the side exhaust ports 138a and 138b located approximately 1.8 inches from the distal end 144. It will be appreciated by the skilled artisan that the number of exhaust ports can be varied, and their location changed, as desired.

Figure 4:
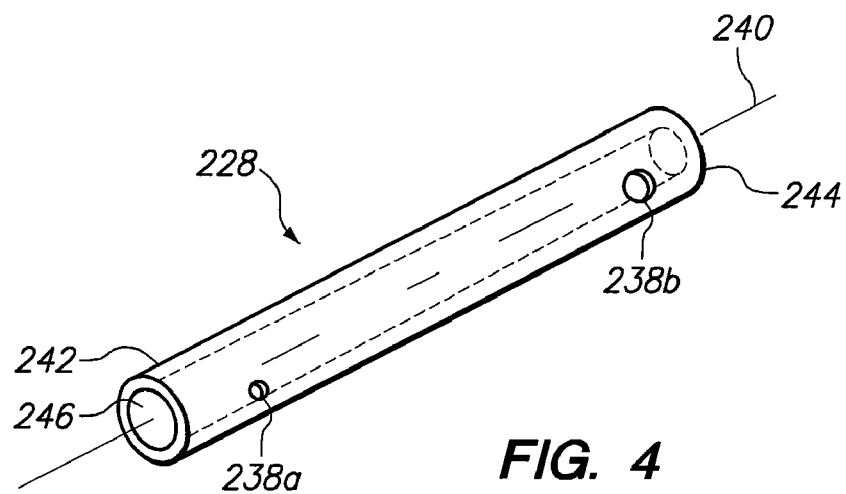
FIG. 4 is a perspective view of another embodiment of a cryoablation segment for use in the catheter shown in FIG. 1 having a lumen that is tapered with a decreasing lumen cross-sectional area in the distal direction.

FIG. 4 shows another embodiment of a cryoablation segment (designated segment 228) for use in the system 10 shown in FIG. 1. As shown in FIG. 4, the segment 228 is shaped as an elongated tube that defines a longitudinal axis 240. For the embodiment shown in FIG. 4, the segment 228 extends from an open proximal end 242 to a closed distal end 244 and is formed with a segment lumen 246 that is tapered with a decreasing lumen cross-sectional area in the distal direction. FIG. 4 further shows that the segment 228 is formed with a distal side exhaust port 238b and a proximal side exhaust port 238a and each exhaust port 238a,b is connected in fluid communication with the tapered lumen 246. Like the embodiments described above, the side exhaust ports 238a,b can be sized to outflow refrigerant through the distal and proximal side exhaust ports 238a,b at a substantially same refrigerant mass flow rate. Moreover, as compared with a uniform, non-tapered lumen, the tapered lumen 246 structure results in less pressure drop as the refrigerant transits to the distal exhaust port 238b. Functionally, the tapered lumen 246 can be employed to prevent boiling of the refrigerant during transit of the refrigerant through the segment 228 to the distal exhaust port 238b. It is to be appreciated that the embodiments for segments 28 and 128 shown in FIGS. 2 and 3 can also use a tapered lumen and that the tapered lumen can be used for segments 28, 128, 228 that have open or closed distal ends 44, 144, 244.

Figure 5:
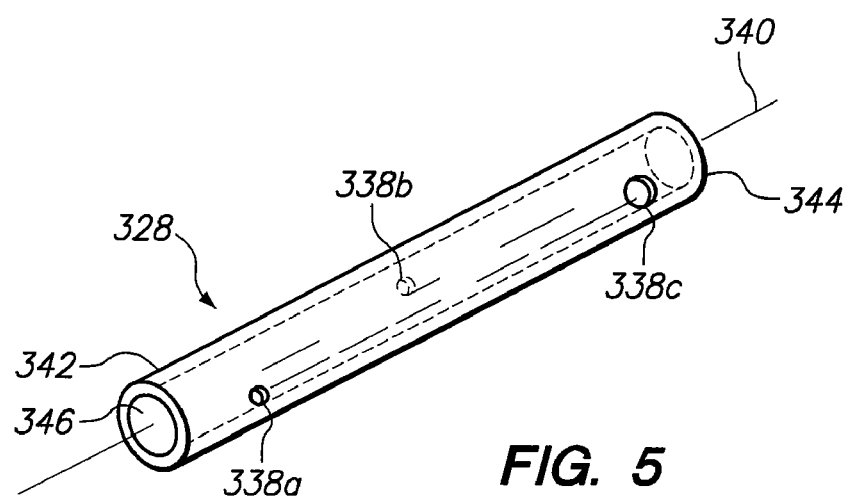
FIG. 5 is a perspective view of another embodiment of a cryoablation segment for use in the catheter shown in FIG. 1 having three side exhaust ports with an intermediate port that is azimuthally offset from the remaining side exhaust ports.

Another embodiment of a cryoablation segment (designated segment 328) is shown in FIG. 5. As seen there, the segment 328 is shaped as an elongated tube that defines a longitudinal axis 340. It can be further seen that the segment 328 extends from an open proximal end 342 to a closed distal end 344 and is formed with a non-tapered segment lumen 346. FIG. 5 further shows that the segment 328 is formed with a distal side exhaust port 338a and a proximal side exhaust port 338c and an intermediate side exhaust port 338b. For the segment 328, each side exhaust port 338a-c is connected in fluid communication with the lumen 346. It can further be seen from FIG. 4 that the intermediate port 338b is azimuthally offset relative to the axis 340 by approximately one-hundred eighty degrees from the side exhaust ports 338a and 338c. Like the embodiments described above, the side exhaust ports 338a-c can be sized to outflow refrigerant through the distal and proximal side exhaust ports 338a-c at a substantially same refrigerant mass flow rate. It will be appreciated, however, that the mass flow rates may differ, depending on the desired effect.

Figure 6:
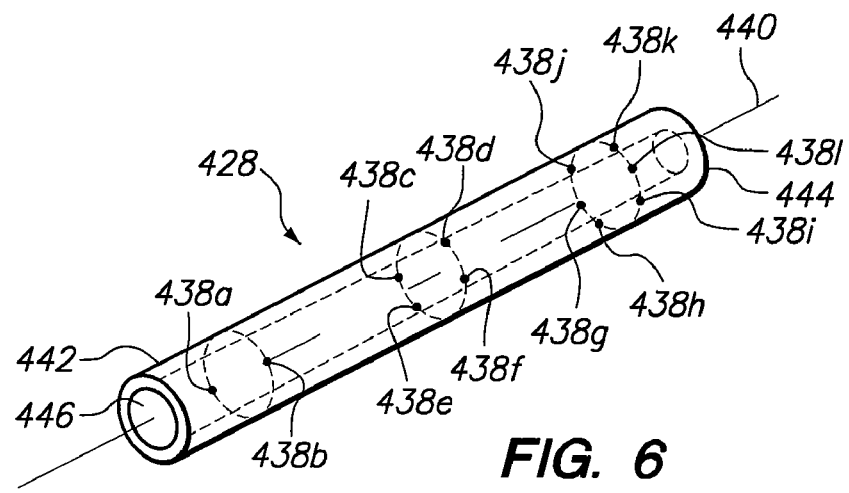
FIG. 6 is a perspective view of another embodiment of a cryoablation segment for use in the catheter shown in FIG. 1 having six side exhaust ports co-located at a first distance from the segment's distal end, four side exhaust ports co-located at a second distance from the segment's distal end and two side exhaust ports co-located at a third distance from the segment's distal end.

FIG. 6 shows another embodiment of a cryoablation segment (designated segment 428) for use in the catheter 12 shown in FIG. 1. As FIG. 6 shows, the segment 428 is shaped as an elongated tube that defines a longitudinal axis 440 and extends from an open proximal end 442 to a closed distal end 444. It can be further seen that the segment 428 is formed with a lumen 446 that is tapered with a decreasing lumen cross-sectional area in the distal direction. FIG. 6 further shows that the segment 428 is formed with twelve distal side exhaust ports 438a-l with each side exhaust port 438a-l connected in fluid communication with the tapered lumen 446. From FIG. 6, it can be seen that two of the side exhaust ports (i.e. ports 438a and 438b) are co-located at a first distance from the segment's distal end 444, four side exhaust ports (i.e. ports 438c-f) are co-located at a second distance from the segment's distal end 444 and six side exhaust ports (i.e. ports 438g-l) are co-located at a third distance from the segment's distal end. Like the embodiments described above, the side exhaust ports 438a-l can be sized to outflow refrigerant through the distal and proximal side exhaust ports 438a-l at a substantially same refrigerant mass flow rate.

While the particular Cryoablation Segment for Creating Linear Lesions and corresponding methods of use as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. A fluid refrigerant delivery system for a cryoablation applicator which comprises:
    a source of fluid refrigerant; and
    a tube shaped cryoablation segment having a proximal end and a distal end with a lumen formed therebetween and with the proximal end operably connected in fluid communication with the fluid refrigerant source, and wherein the segment is formed with a first exhaust port and a second exhaust port with the second exhaust port positioned distal to the first exhaust port, wherein the first exhaust port has a port diameter D and the second exhaust port has a port diameter d, with the second exhaust port diameter being larger than the first exhaust port diameter (d>D), such that the segment is configured to outflow fluid refrigerant at the first and second exhaust ports at substantially the same refrigerant mass flow rates for subsequent transition of the fluid refrigerant from a liquid state to a gaseous state.

2. A system as recited in claim 1 wherein the lumen is in fluid communication with each exhaust port and the lumen is tapered with a decreasing lumen cross-sectional area in the distal direction.

3. A system as recited in claim 1 further comprising a third exhaust port with the third exhaust port being at a same distance from the distal end as the first exhaust port.

4. A system as recited in claim 3 wherein the first exhaust port is positioned diametrically opposite the third exhaust port.

5. A system as recited in claim 1 wherein the second exhaust port is an end exhaust port positioned at the distal end of the tube.

6. A system as recited in claim 1 wherein the segment is formed with at least one intermediate exhaust port between the first exhaust port and the second exhaust port.

7. A system as recited in claim 6 wherein the segment is formed with an end exhaust port positioned at the distal end of the tube, the end exhaust port has a diameter of approximately 0.008 inches, the second exhaust port has a diameter of approximately 0.005 inches, the intermediate exhaust port has a diameter of approximately 0.004 inches, and the first exhaust port has a diameter of approximately 0.003 inches.

8. A system as recited in claim 1 wherein the tubular segment defines a longitudinal axis and the first exhaust port is azimuthally offset relative to the axis from the second exhaust port.

9. A system as recited in claim 1 wherein the tubular segment is further formed with a third exhaust port with the first, second and third exhaust ports being positioned along a common linear axis and the segment is configured to outflow refrigerant at the first, second and third exhaust ports at a substantially same refrigerant mass flow rate.

10. A system as recited in claim 1 wherein the applicator is a probe.

11. A system as recited in claim 1 wherein the applicator is a catheter.

12. A fluid refrigerant delivery system for a cryoablation applicator which comprises:
   a source of fluid refrigerant;
   an elongated cryoablation segment having a length and a lumen extending therethrough, the segment formed with a plurality of fluid exhaust ports, wherein the lumen is in fluid communication with each exhaust port and the lumen is tapered with a decreasing lumen cross-sectional area in a distal direction, with the lumen of the segment connected in fluid communication with the source of fluid refrigerant; and
   a means for passing the fluid refrigerant through the lumen of the cryoablation segment for simultaneous exit therefrom through each of the plurality of exhaust ports in a liquid state and at substantially the same mass flow rates for subsequent transition from a liquid state into a gaseous state.

13. A system as recited in claim 12 wherein the length of the segment is approximately two inches.

14. A system as recited in claim 12 wherein the segment is made of nylon.

15. A system as recited in claim 12 wherein the segment is tubular shaped, has a proximal end and a distal end, and is formed with an end exhaust port at the distal end and a plurality of side exhaust ports arranged as diametrically opposed pairs and positioned in pairs along the length of the segment.

16. A system as recited in claim 15 wherein the plurality of side exhaust ports comprises:
   a distal pair of side exhaust ports;
   an intermediate pair of side exhaust ports located proximal the distal pair; and
   a proximal pair of side exhaust ports located proximal the intermediate pair.

17. A system as recited in claim 16 wherein the side exhaust ports of each pair have a same diameter.

18. A system as recited in claim 16 wherein the end exhaust port has a diameter of approximately 0.008 inches, the side exhaust ports of the distal pair each have a diameter of approximately 0.005 inches, the side exhaust ports of the intermediate pair each have a diameter of approximately 0.004 inches, and the side exhaust ports of the proximal pair each have a diameter of approximately 0.003 inches.

19. A method for cooling an elongated cryoablation segment which comprises the steps of:
   providing a source of fluid refrigerant;
   connecting a tube shaped cryoablation segment having a proximal end and a distal end with a lumen formed therebetween in fluid communication with the fluid refrigerant source, wherein the tube is formed with an end exhaust port at the distal end of the segment and a plurality of side exhaust ports located between the proximal end and the distal end of the segment, wherein a first exhaust port has a port diameter D and a second exhaust port has a port diameter d, with the second exhaust port diameter being larger than the first exhaust port diameter (d>D), wherein the second exhaust port is distal of the first exhaust port; and
   passing the fluid refrigerant through the cryoablation segment for simultaneous exit therefrom through the end exhaust port and through each of the side exhaust ports in a liquid state and at substantially the same mass flow rates for subsequent transition from a liquid state into a gaseous state.

20. A method as recited in claim 19 wherein the segment has a length between the distal end and the proximal end and the plurality of side exhaust ports are arranged as diametrically opposed pairs and positioned in pairs along the length of the segment.

21. A method as recited in claim 20 wherein the plurality of side exhaust ports comprises:
   a distal pair of side exhaust ports;
   an intermediate pair of side exhaust ports located proximal the distal pair; and
   a proximal pair of side exhaust ports located proximal the intermediate pair, and wherein the end exhaust port has a diameter of approximately 0.008 inches, the side exhaust ports of the distal pair each have a diameter of approximately 0.005 inches, the side exhaust ports of the intermediate pair each have a diameter of approximately 0.004 inches, and the side exhaust ports of the proximal pair each have a diameter of approximately 0.003 inches.

\* \* \* \* \*